(12) United States Patent
Brown, Sr.

(10) Patent No.: US 10,849,367 B2
(45) Date of Patent: Dec. 1, 2020

(54) UNIVERSAL SEPARATION PANEL FOR USE IN MEN'S CLOTHING

(71) Applicant: Gregory S. Brown, Sr., Ellicott City, MD (US)

(72) Inventor: Gregory S. Brown, Sr., Ellicott City, MD (US)

(*) Notice: Subject to any disclaimer, the term of this patent is extended or adjusted under 35 U.S.C. 154(b) by 0 days.

(21) Appl. No.: 16/207,861

(22) Filed: Dec. 3, 2018

(65) Prior Publication Data
US 2020/0015526 A1 Jan. 16, 2020

Related U.S. Application Data

(60) Provisional application No. 62/697,756, filed on Jul. 13, 2018.

(51) Int. Cl.
*A41B 9/02* (2006.01)
*A61F 13/15* (2006.01)
*A41C 5/00* (2006.01)

(52) U.S. Cl.
CPC .............. *A41B 9/023* (2013.01); *A61F 13/15* (2013.01); *A41C 5/00* (2013.01)

(58) Field of Classification Search
CPC .......... A41B 9/023; A41B 9/00; A41B 9/026; A61F 13/15
USPC .................................................... 2/403, 405
See application file for complete search history.

(56) References Cited

U.S. PATENT DOCUMENTS

| | | | | |
|---|---|---|---|---|
| 2,235,849 A | * | 3/1941 | Reis .......................... | A41B 9/02 2/234 |
| 2,601,602 A | * | 6/1952 | Firsching, Sr. ......... | A41B 9/023 602/67 |
| 3,844,282 A | * | 10/1974 | King ....................... | A41B 9/023 602/67 |
| 4,961,419 A | * | 10/1990 | Tribble ................... | A41B 9/023 2/403 |
| 5,647,065 A | * | 7/1997 | Richerson .............. | A41B 9/023 2/227 |
| 5,718,003 A | * | 2/1998 | Gwinn .................... | A41B 9/023 2/400 |
| 8,726,423 B2 | * | 5/2014 | Gu ......................... | A41B 9/023 2/404 |
| 8,782,817 B2 | * | 7/2014 | Gu ......................... | A41B 9/002 2/405 |
| 9,082,660 B2 | * | 7/2015 | Feng ....................... | H01L 22/12 |
| 2004/0154078 A1 | * | 8/2004 | Auger .................... | A41B 9/023 2/400 |
| 2006/0000008 A1 | * | 1/2006 | Chong .................... | A41B 9/023 2/403 |
| 2007/0277285 A1 | * | 12/2007 | Gravette ................. | A41B 9/023 2/78.1 |
| 2012/0260404 A1 | * | 10/2012 | Steele .................... | A41B 9/023 2/404 |
| 2013/0104293 A1 | * | 5/2013 | Gu ......................... | A41B 9/023 2/404 |

(Continued)

*Primary Examiner* — Gloria M Hale
(74) *Attorney, Agent, or Firm* — Sughrue Mion, PLLC

(57) ABSTRACT

A garment panel includes a material that is configured to attach to an internal surface of a garment to form the garment panel, and that includes a front surface and a rear surface; and an opening in the material to permit genitalia of a user to be inserted through the opening and remain disposed in a space formed between the internal surface of the garment and the front surface of the material.

21 Claims, 6 Drawing Sheets

(56) References Cited

U.S. PATENT DOCUMENTS

2013/0219591 A1\* 8/2013 Gu .................. A41B 9/023
 2/405
2019/0110523 A1\* 4/2019 Gu .................. A41B 9/023

\* cited by examiner

UNIVERSAL SEPARATION PANEL FOR USE IN MEN'S CLOTHING

CROSS-REFERENCE TO RELATED APPLICATION

This application claims priority under 35 U.S.C. § 119 to U.S. Provisional Application No. 62/697,756, filed on Jul. 13, 2018, the contents of which are incorporated by reference in their entirety.

FIELD

The present disclosure generally relates to an accessory that is attached to a garment worn around the genitalia area of a user. This disclosure includes a separation panel that supports the genitalia of a male while keeping them away from the user's skin.

BACKGROUND

Traditional underwear does not have any additional component that focuses on the comfortability of the genitalia. This results in the genitalia adhering to the legs and perineum region of the skin due to sweat and the like. Previous attempts at solving this issue have failed in two major aspects: firstly, they have focused on brief type of underwear, and secondly, they do not provide sustained separation of the genitalia from the perineum region. While sitting, the scrotum often comes into contact with the thighs and the perineum region resulting in sweat and stickiness. In the pursuit of very comfortable boxer type of underwear a separation panel has been developed.

SUMMARY

The present disclosure involves a separation panel that supports the user's genitalia. The present disclosure includes a pass-through port, formed entirely within the separation panel, which allows the user to pass through the genitalia into the containment area, and a slack opening for placement and inspection.

The following are some of the problems the present disclosure is designed to solve: skin on skin contact, most notably scrotum to thighs and scrotum to the perineum region; and a method to prevent the scrotum from moving down between the legs and in the perineum region, which is coincidentally between the thighs; providing a containment area that contains minor drips and dribbles, and that keeps the penis in the containment area while simultaneously allowing it to be easily and quickly located, such as when locating the penis and maneuvering it out of the underwear for the purpose of urination.

Further, if the genitalia routinely slip out of the containment area, the garment no longer provides the separation. The pulling and tugging, due to for example running and moving, of the underwear often results in the genitalia slipping out of the containment area. The present disclosure is designed to prevent the genitalia from slipping out.

An objective of the present disclosure is to ensure the genitalia are adequately separated from the perineum region. The present disclosure has been tested and provides excellent levels of comfort, separation and gentle support. The separation panel can be fitted into most men's and boy's undergarments and outer garments of the lower torso type, without significantly modifying the garment. Simply attaching the present disclosure to the inside of an appropriate garment renders the present disclosure useable. These garments can include all styles of clothing, including but not limited to underwear from boxers, to briefs, to boxer briefs; all types of pajamas, long underwear, jogging pants, running pants, hiking and sports pants. Thus, the present disclosure provides universal usability. The present disclosure enhances a traditional garment such as a pair of boxers to provide a separate containment area for the genitalia with gentle support and ample space for a comfortable free and open feeling, in a manner that maintains separation even in vigorous activities. The design of the present disclosure ensures continuous gentle support for comfort and skin health and the protection from drips or dribbles going down the leg, following urination and perhaps due to mild incontinence. The design is also easy to manufacture for any men's and boy's garment such as underwear, shorts of many types, pajama pants, and many types of pants. A feature of the panel installed in a loose fitting garment such as boxer shorts is the panel being open across the top and stitched across the bottom and partially up the sides which will contain and absorb minor drips or dribble, like occurs after urination. The open top and upper sides allows for easy insertion, placement and inspection of the genitalia into the containment area. The design also includes the facility to insert a leak protective pad that will stay in place for absorbing more serious leakage.

DETAILED DESCRIPTION

Figure 1:
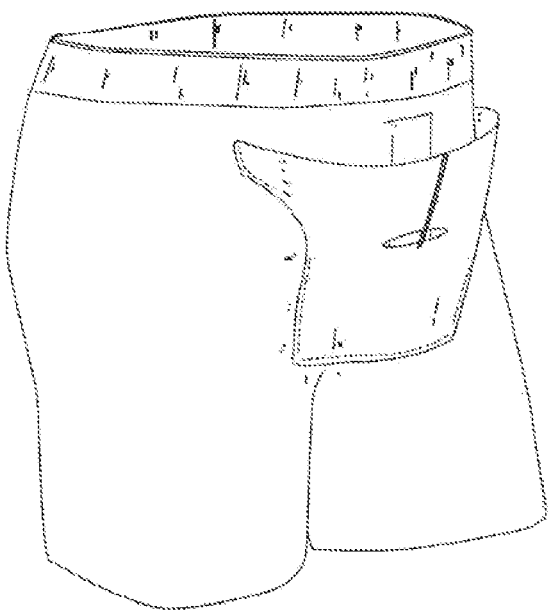
FIG. 1 is a perspective view of the present disclosure, shown inside out.
Figure 2:
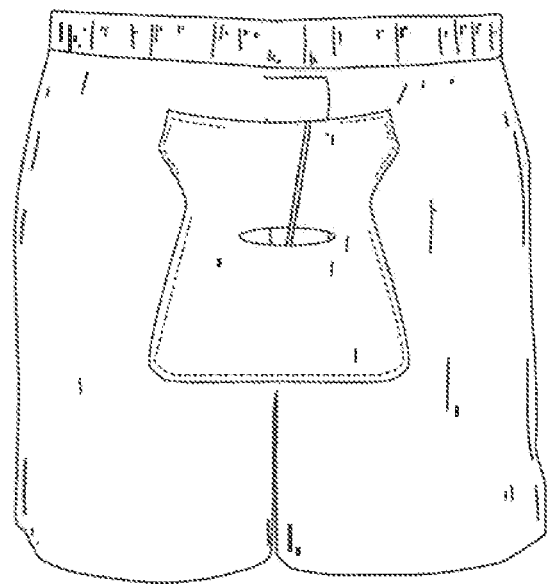
FIG. 2 is a front view of the present disclosure, shown inside out.
Figure 3:
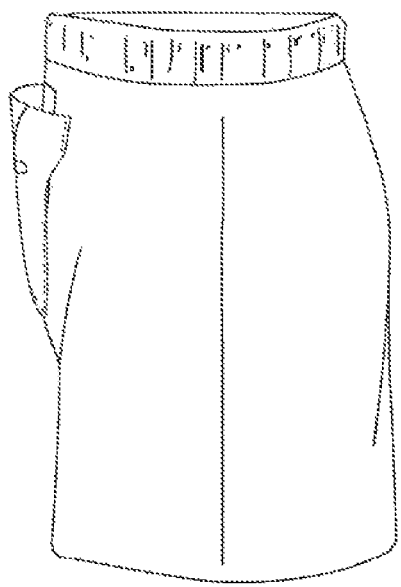
FIG. 3 is a right view of the present disclosure, shown inside out.

All illustrations of the drawings are for the purpose of describing selected versions of the present disclosure and are not intended to limit the scope of the present disclosure. FIG. 1 shows an embodiment of the present disclosure that comprises an upper end, a lower end, a first side, a second side, a pass-through port, a containment area, and a slack opening. The present disclosure is a panel, preferably made of a fabric, that is placed on the interior of a garment on the garment's genitalia area. A preferred embodiment of the separation panel is a trapezoidal shape with the upper end and lower end parallel to each other. The upper end is the longer of the two parallel ends of the trapezoid, with the lower end being the shorter end. As seen in FIG. 2, the first side and the second side are the same length and connect the upper end and lower end to each other. In reference to FIG. 2, the pass-through port is an elliptical hole located towards the upper end of the present disclosure.

In a preferred embodiment, the length of the upper end is equivalent to twice the length of the fly opening of the garment to which the separation panel is attached. However the upper end is not limited to this length and can range anywhere between 100% and 300% of the length of the fly opening.

The upper end is longer than the lower end. The first side and second side have an equivalent length that is longer than the length of the lower end.

Figure 6:
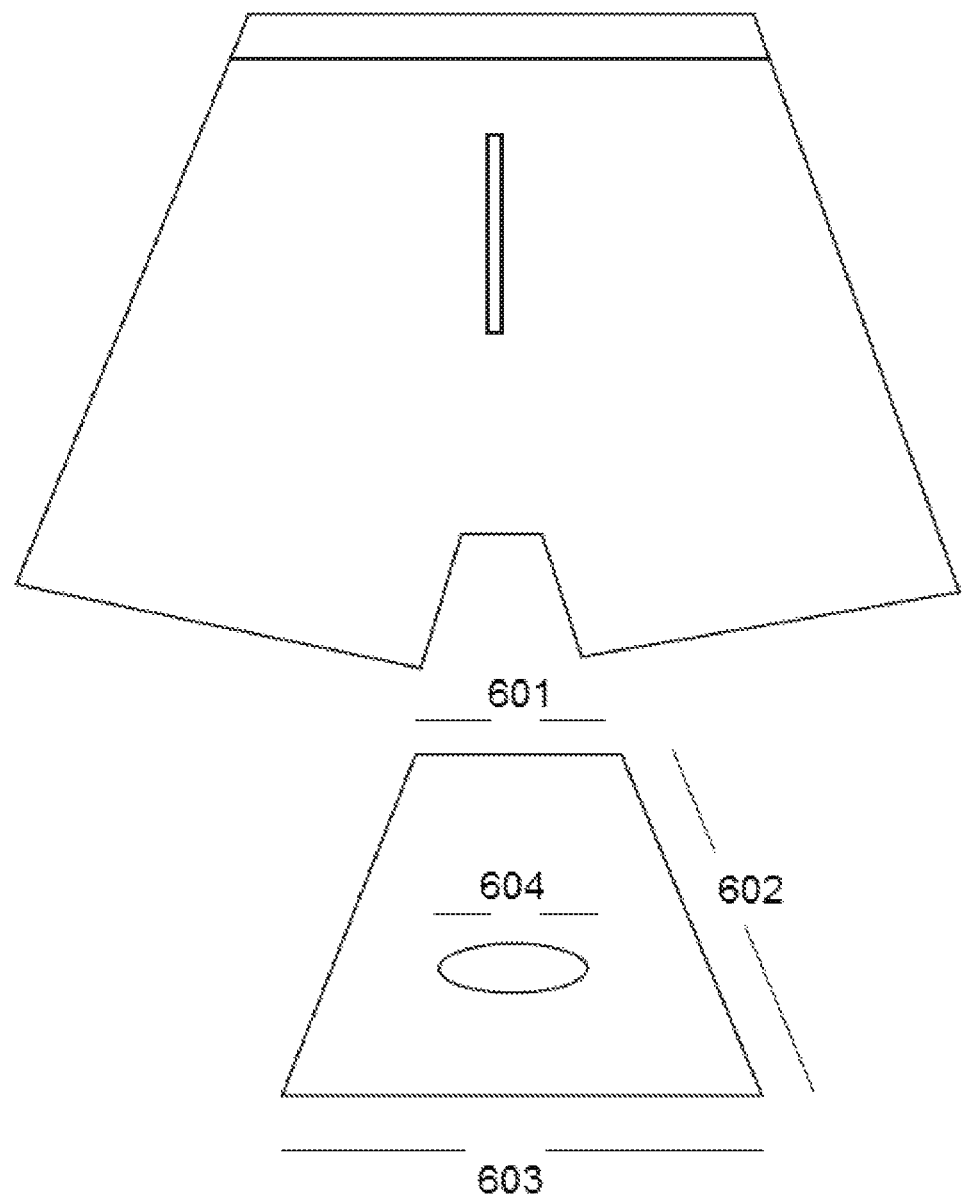
FIG. 6 is a diagram of a front view of the separation panel and an undergarment before being assembled.
Figure 7:
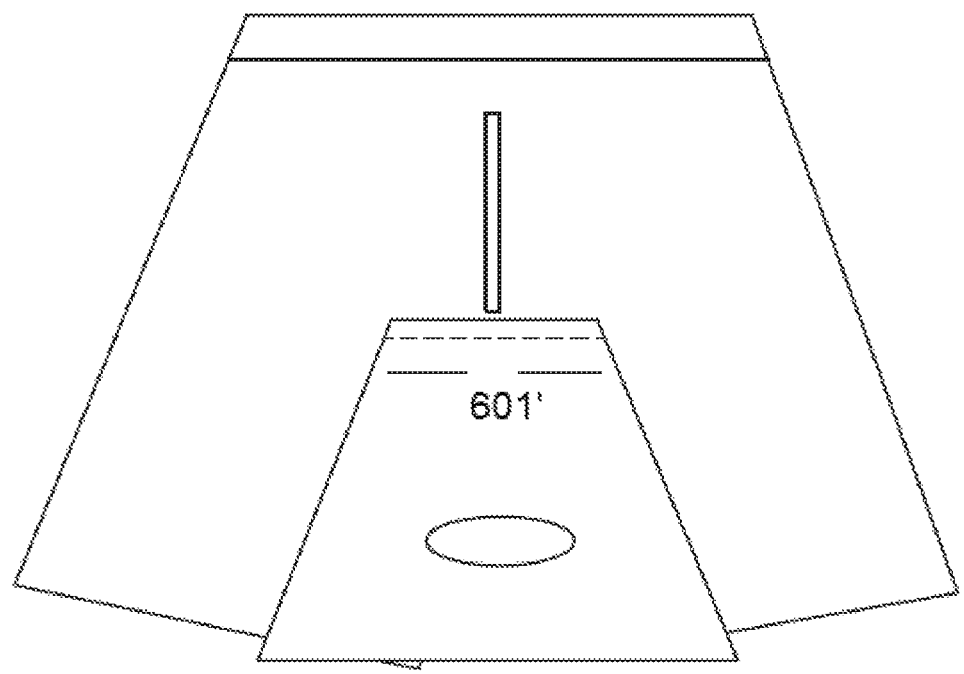
FIG. 7 is a diagram of a front view of the separation panel and an undergarment, when partially assembled, shown inside out.

As shown in FIG. 6, the length of the upper end 603 is preferably 100% longer than the length of lower end 601 but can range between 100% and 300% longer. The length of the first and second sides 602 are preferably 150% longer than the lower end 601 but can range between 100% and 200% longer. The lower end 601 is typically the length of the fly and can range from 50% to 150% the length of the fly. The length of pass-through port 604 is typically 70% of the length of the fly and can range between 30% and 150%. As shown in FIG. 7, the entire length of the bottom side 601' is attached to the garment.

The present disclosure can be constructed in various sizes and shapes, thus is not limited to a trapezoid shape. For example, the separation panel could be rectangular or triangular.

The pass-through port has an elliptical shape that is horizontal in the embodiment shown; however it is not limited to this orientation. Further, the pass-through port is not limited to an elliptical shape. For example, the pass through port could be a simple incision in the separation panel or any geometric shape such as a triangle or a quadrangle.

In a preferred embodiment, an elastic component travels over the pass-through port. The elastic component comprises an elastic first end and an elastic second end. The elastic first end attaches to the separation panel between the pass-through port and the upper end and the second end attaches near a lower side of the pass-through port. As seen in FIG. 2, the elastic component travels directly over the pass-through hole and attaches to the upper end. In a preferred embodiment, the elastic component is attached to the upper end at a position away from the center of the upper end. The elastic component is a string or band that is made from any elastic material and can be covered in fabric. The elastic first end and elastic second end are attached using stitching in a preferred embodiment; however any means of adherence can also be used. Another embodiment of the separation panel may not include the elastic component.

The pass-through port is positioned to be generally aligned in the center of the fly of the garment. That is, the pass-through port is located roughly equidistant between the first side and the second side. The center of pass-through port is also preferably located closer to the upper end than the lower end. However, the pass through port can be located anywhere between the upper end and the lower end. The pass-thru port can be elasticized in the stitching or fitted with elastic to make the port an elastic opening.

In a preferred embodiment, the present disclosure is adhered to the garment using stitching. The corners that are formed at the intersection of the upper end and the first and second sides features first end stitching's as illustratively seen in FIG. 2.

Figure 8:
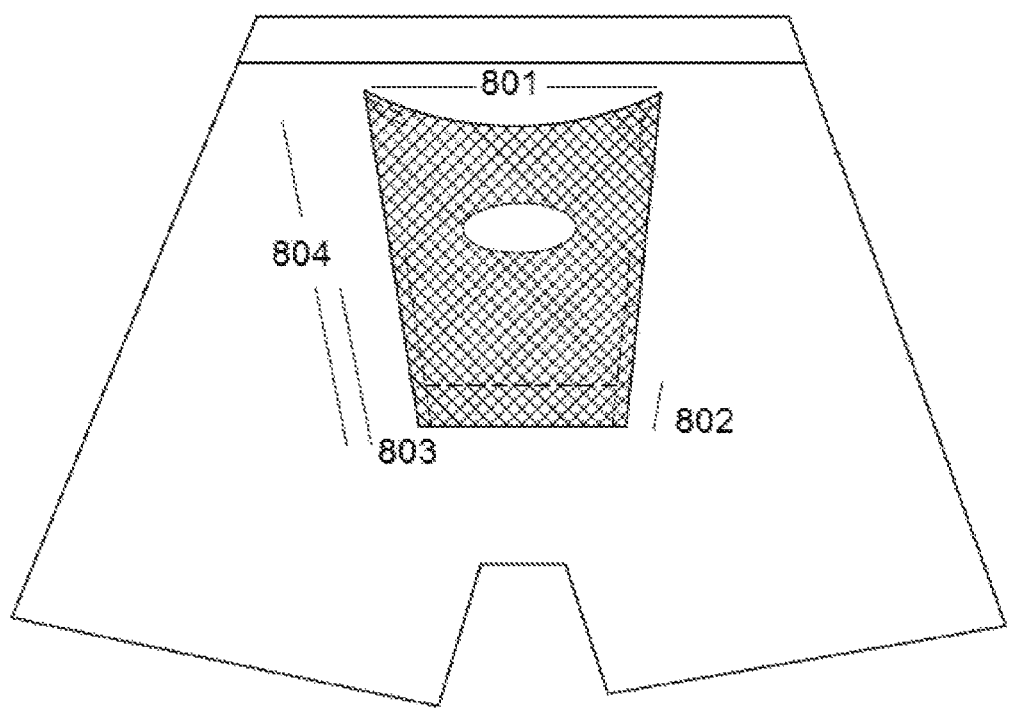
FIG. 8 is a diagram of a front view of the separation panel and an undergarment, after being assembled, shown inside out.

FIG. 8 shows the first end stitching's. The combined length of the first end stitching's are preferably 5% of the length across the upper end of the panel 801. However, the combined length of the first end stitches maybe be as much as 30% the length across the upper end of the panel 801 or as little as a minimum length needed to secure the panel.

Parallel to the lower end is a second end stitching. The second end stitching lines the length of the second end. The second end stitching is provided along the edge. A distance 802 is formed by the fabric being folded over and up, typically 20% of the side and can be as little as 10% to as much as 30%. This fold over is what provides the supporting platform for the genitalia to rest and provide gentle support.

The first side includes a first side stitching that lines the lower half of the first side. FIG. 8 shows the length of first side stitching 803. In a preferred embodiment the length of the first side 804 is 100% larger than the length of the first side stitching 803. The length of the first side 804 is not limited to being 100% larger than the length of the first side stitching 803 and can range anywhere between 50% and 200% larger than the length of the first side stitching 803.

The first end stitching intersects the end of the second side stitching and ends at the lower end, as can illustratively be seen in FIG. 2. The second side stitching is a mirror of the first side stitching and is located parallel to the second side. The opening on the first side and second side adjacent to the stitching along with the opening across the top allows the user to insert and adjust their genitalia while donning and wearing the garment.

Figure 4:
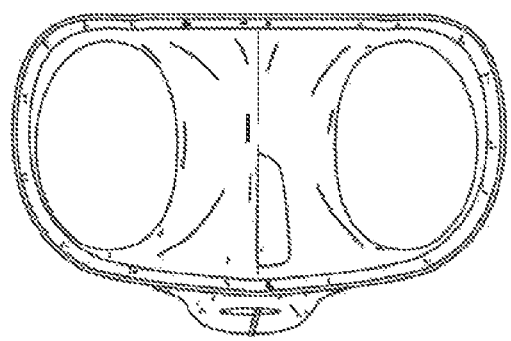
FIG. 4 is a top view of the present disclosure, shown inside out.
Figure 5:
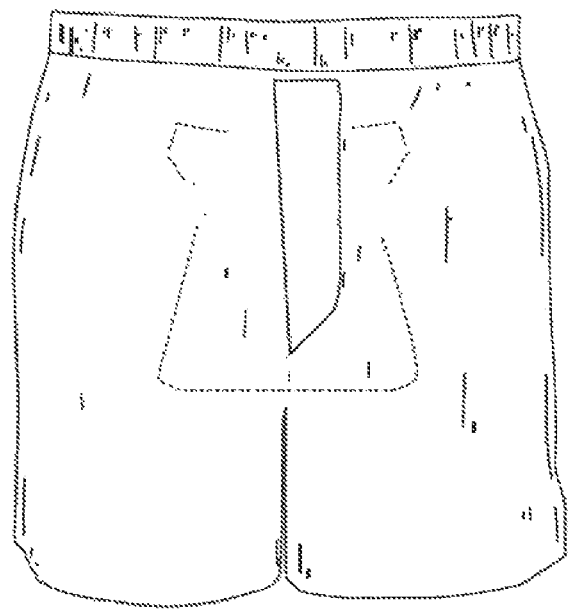
FIG. 5 is a front view of the traditional boxer with the disclosure installed.

When the present disclosure is attached to a garment, the area between the present disclosure and the garment is a containment area, as seen in FIG. 4. The figure shows the garment inside out. Upon wearing, right side in, the garment with the present disclosure attached, the user inserts their scrotum and penis through the pass-through port, which has a width dimension 604, into the containment area While doing this, the user extends the elastic component to open up the pass-through port. When the genitalia are fully inserted into the containment area, the user releases the elastic member, which ensures the pass-through port remains tight enough to prevent the genitalia from slipping out of the containment area. The unstitched section on the upper end and upper sides provides for easy insertion, positioning and inspection.

This unstitched section that creates a slack opening will now be discussed. The panel's dimensions and position of the attachment points creates a size difference between the length of the upper end of the separation panel C and the distance between the attachment points on the material to which the upper end is attached C'.

FIG. 8 shows, in a preferred embodiment, the length across the upper end of the panel C is 30% larger than the distance between the attachments points on the short C'. However the length ratio is not limited to 30% and can range anywhere between 10% and 100%.

The slack in the open top, as well as, the partially open sides allows for the wearer to easily position the genitalia through the pass-thru port. The hands can work either from the sides and/or top and there is visibility from the top. The panel's dimensions being larger than the attachment points creates slack that provides a panel that moves with the body and the base of the genitalia and not with the underwear.

When installing the separation panel into the garment, the second end stitching is completed before the first and second side stitching. Installing the separation panel in this manner, combined with the slack discussed above, creates a loose supporting platform in the bottom of the containment area which improves the user's comfort.

The containment area may also function as a housing for an absorbent pad. This pad, as well as the containment area, can soak up leakage from the penis, commonly occurring after urination or perhaps due to mild incontinence. This prevents leakage from traveling down the leg of the user and being absorbed by clothing, which can be evident to others due to the formation of a wet spot.

Although the disclosure has been explained in relation to its preferred embodiment, it is to be understood that many other possible modifications and variations can be made without departing from the spirit and scope of the disclosure.

What is claimed is:

1. A garment panel, comprising:
a material that is configured to attach to an internal surface of a garment to form the garment panel, and that includes a front surface and a rear surface; and
an opening in the material to permit genitalia of a user to be inserted through the opening and remain disposed in a space formed between the internal surface of the garment and the front surface of the material,
wherein the material includes a top side that is partially attached to the internal surface of the garment to form a top gap between the material and the internal surface of the garment.

2. The garment panel of claim 1, wherein the material is configured to attach to the internal surface at a bottom side of the material and the top side of the material to permit slack in a vertical direction and a horizontal direction.

3. The garment panel of claim 1, wherein an entire bottom side of the material is attached to the internal surface of the garment, and wherein respective corners of the top side of the material are attached to the internal surface of the garment to form the top gap formed in a vertical direction between the material and the internal surface of the garment.

4. The garment panel of claim 1, wherein the opening is formed of at least one of a circle, an oval, a triangle, square, diamond, trapezoid or slit and can be vertically or horizontally disposed.

5. The garment panel of claim 1, wherein a bottom side of the material coincides with a bottom portion of a fly of the garment to permit the genitalia to rest on an area adjacent to the bottom side on the front surface of the material.

6. The garment panel of claim 1, wherein the material is attached to the internal surface of the garment along an entire bottom side of the material, and is partially attached to the internal surface along the left side and the right side of the material to form respective side gaps.

7. The garment panel of claim 1, wherein an amount of slack associated with the material is different than an amount of slack formed by the garment.

8. The garment panel of claim 1, wherein the material is configured to permit an absorbent pad to be inserted in the space formed between the internal surface of the garment and the front surface of the material.

9. The garment panel of claim 1, wherein the material is formed of a synthetic material, a cloth material, or a mesh.

10. The garment panel of claim 1, wherein the garment is at least one of an undergarment, a pant, or a short.

11. A garment, comprising:
a main garment portion configured to be worn by a user, and that includes an external surface and an internal surface; and
a material forming a panel portion attached to the internal surface of the main garment portion, and that includes a front surface and a rear surface, and
wherein the panel portion further includes an opening to permit genitalia of the user to be inserted through the opening and remain disposed in a space formed between the internal surface of the main garment portion and the front surface of the panel portion, and
wherein the material includes a top side that is partially attached to the internal surface of the main garment portion to form a top gap between the material and the internal surface of the main garment portion.

12. The garment of claim 11, wherein the material is configured to attach to the internal surface at a bottom side of the material and the top side of the material to permit slack in a vertical direction and a horizontal direction.

13. The garment of claim 11, wherein an entire bottom portion of the material is attached to the internal surface of the main garment portion, and wherein respective corners of the top side of the material are attached to the internal surface of the main garment portion to form the top gap formed in a vertical direction between the material and the internal surface of the main garment portion.

14. The garment of claim 11, wherein the opening is formed of at least one of a circle, an oval, square, triangle, diamond, trapezoid or slit vertically or horizontally disposed.

15. The garment of claim 11, wherein a bottom side of the material coincides with a bottom portion of a fly of the garment to permit the genitalia to rest on an area adjacent the bottom side on the front surface of the material.

16. The garment of claim 11, wherein the material is attached to the internal surface of the main garment pin portion along an entire bottom side of the material, and is partially attached to the internal surface along the left side and the right side of the material to form respective side gaps.

17. The garment of claim 11, wherein an amount of slack associated with the material is different than an amount of slack formed by the garment.

18. The garment of claim 11, wherein the material is configured to permit an absorbent pad to be inserted in the space formed between the internal surface of the main garment portion and the front surface of the material.

19. The garment of claim 11, wherein the material is formed of a synthetic material, a cloth material, or a mesh.

20. The garment panel of claim 1, wherein the opening includes an elastic portion.

21. The garment of claim 11, wherein the opening includes an elastic portion.

* * * * *